(12) United States Patent
Henneken et al.

(10) Patent No.: US 10,828,673 B2
(45) Date of Patent: Nov. 10, 2020

(54) ULTRASOUND TRANSDUCER ARRANGEMENT AND ASSEMBLY, COAXIAL WIRE ASSEMBLY, ULTRASOUND PROBE AND ULTRASONIC IMAGING SYSTEM

(71) Applicant: KONINKLIJKE PHILIPS N.V., Eindhoven (NL)

(72) Inventors: Vincent Adrianus Henneken, Eindhoven (NL); Marcus Cornelis Louwerse, Eindhoven (NL); Johannes Wilhelmus Weekamp, Eindhoven (NL); Ronald Dekker, Eindhoven (NL); Marc Godfriedus Marie Notten, Eindhoven (NL); Antonia Cornelia Jeannet Van Rens, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 624 days.

(21) Appl. No.: 15/326,055

(22) PCT Filed: Jun. 25, 2015

(86) PCT No.: PCT/EP2015/064365
§ 371 (c)(1),
(2) Date: Jan. 13, 2017

(87) PCT Pub. No.: WO2016/008690
PCT Pub. Date: Jan. 21, 2016

(65) Prior Publication Data
US 2017/0209898 A1 Jul. 27, 2017

(30) Foreign Application Priority Data

Jul. 17, 2014 (EP) ..................... 14177454

(51) Int. Cl.
*B06B 1/02* (2006.01)
*A61B 8/00* (2006.01)
(Continued)

(52) U.S. Cl.
CPC ............. *B06B 1/0292* (2013.01); *A61B 8/12* (2013.01); *A61B 8/445* (2013.01); *A61B 8/4494* (2013.01);
(Continued)

(58) Field of Classification Search
CPC ... B06B 1/0292; B06B 1/0622; B06B 1/0688; A61B 8/445; A61B 8/4494
See application file for complete search history.

(56) References Cited

U.S. PATENT DOCUMENTS 5,857,974 A 1/1999 Eberle et al.
5,997,479 A 12/1999 Savord et al.
(Continued)

FOREIGN PATENT DOCUMENTS

CN 1930689 A 3/2007
CN 101270345 A 9/2008
(Continued)

OTHER PUBLICATIONS

Nongaillard et al "Design for Manufacturing of Low Voltage Three Dimensioinal Capacitors" IEEE Transactinons on Device and Materials Reliability vol. 10 No. 3, Sep. 2010 p. 396-402.
(Continued)

*Primary Examiner* — George R Evanisko

(57) ABSTRACT

An ultrasound transducer arrangement (100) is disclosed comprising a plurality of substrate islands (110, 120, 130) spatially separated and electrically interconnected by a flexible polymer assembly (150) including electrically conductive tracks providing said electrical interconnections, said plurality including a first substrate island (110) comprising
(Continued)

a plurality of ultra sound transducer cells (112) and a second substrate island (120) comprising an array of external contacts for connecting the ultrasound sensor arrangement to a flexible tubular body including a coaxial wire assembly (200) comprising a plurality of coaxial wires (220) each having a conductive core (228) covered by an electrically insulating sleeve (226); and an electrically insulating body (210) having a first main surface (211), a second main surface (213) and a plurality of through holes (212) each extending from the first main surface to the second main surface and coated with an electrically conductive member, wherein each coaxial wire comprises an exposed terminal core portion mounted in one of said though holes from the first main surface, and wherein each through hole is sealed by a solder bump (214) on the second main surface such that the ultrasound transducer arrangement can be directly mounted on the flexible tubular body without the need for a PCB.

12 Claims, 11 Drawing Sheets

(51) Int. Cl.
  *B06B 1/06* (2006.01)
  *A61B 8/12* (2006.01)
  *H01R 4/02* (2006.01)
  *H01R 12/51* (2011.01)
(52) U.S. Cl.
  CPC ........... *B06B 1/0622* (2013.01); *H01R 4/023* (2013.01); *H01R 12/515* (2013.01)

(56) References Cited

U.S. PATENT DOCUMENTS

| | | | |
|---|---|---|---|
| 6,013,032 A | 1/2000 | Savord | |
| 6,443,896 B1 | 9/2002 | Detmer | |
| 6,530,885 B1 | 3/2003 | Entrekin et al. | |
| 6,618,916 B1* | 9/2003 | Eberle | A61B 1/0011 |
| | | | 264/272.11 |
| 6,623,432 B2 | 9/2003 | Powers et al. | |
| 8,360,807 B2 | 1/2013 | Buff et al. | |
| 9,408,588 B2 | 8/2016 | Huang et al. | |
| 10,192,281 B2 | 1/2019 | Boles et al. | |
| 10,238,364 B2 | 3/2019 | Deladi et al. | |
| 2002/0087083 A1* | 7/2002 | Nix | A61B 8/12 |
| | | | 600/459 |
| 2003/0236443 A1 | 12/2003 | Cespedes | |
| 2004/0054289 A1 | 3/2004 | Eberle et al. | |
| 2010/0280388 A1 | 11/2010 | Huang | |
| 2014/0148703 A1* | 5/2014 | Deladi | A61B 8/0883 |
| | | | 600/459 |

FOREIGN PATENT DOCUMENTS

| | | |
|---|---|---|
| CN | 101960673 A | 1/2011 |
| JP | 4179074 A | 6/1992 |
| JP | 2001178724 A | 7/2001 |
| JP | 2005334306 A | 12/2005 |
| JP | 2008153403 A | 7/2008 |
| WO | 2005088725 A2 | 9/2005 |

OTHER PUBLICATIONS

Nongaillard et al "Design for Manufacturing of 3D Capacitors" Microelectronics Journal 41 (2010) p. 845-850.

Integraed Passive Devices Technology Breakthrough by IPDIA (White Paper) Rev 1.1. Released Jan. 7, 2010.

Mimoun et al "Flex to Rigid (F2R) a Novel Ultra-Flexible Technology for Smark Invasive Medical Instruments" Stetchable Electronics and Conformal Biointerfaces, Mater, Res. Soc. Symp. Proc. vol. 1271E, 2010.

Chengwen Pei et al: "A novel, low-cost deep trench decoupling capacitor for high-performance, low-power bulk CMOS applications-",Solid-State and Integrated-Circuit Technology, 2008. ICSICT 2008. 9th International Conference on, IEEE,Piscatawav, NJ, USA, Oct. 20, 2008 (Oct. 20, 2008), pp. 1146-1149.

* cited by examiner (d)

(e)

(f)

ULTRASOUND TRANSDUCER ARRANGEMENT AND ASSEMBLY, COAXIAL WIRE ASSEMBLY, ULTRASOUND PROBE AND ULTRASONIC IMAGING SYSTEM

This application is the U.S. National Phase application under 35 U.S.C. § 371 of International Application No. PCT/EP2015/064365, filed on Jun. 25, 2015, which claims the benefit of EP Application Serial No. 14177454.7 filed Jul. 17, 2014. These applications are hereby incorporated by reference herein.

FIELD OF THE INVENTION

The present invention relates to an ultrasound transducer arrangement comprising a plurality of substrate islands spatially separated and electrically interconnected by a flexible polymer assembly.

The present invention further relates to an ultrasound transducer assembly including such an ultrasound transducer arrangement.

The present invention yet further relates to a coaxial wire assembly for mating with the ultrasound transducer assembly.

The present invention still further relates to an ultrasound probe including such an ultrasound transducer assembly and coaxial wire assembly.

The present invention even still further relates to an ultrasound imaging system including such an ultrasound probe.

BACKGROUND OF THE INVENTION

IC dies including ultrasound sensing capabilities, e.g. ultrasonic transducer chips, are increasingly used as a sensing tip of an ultrasound probe such as an ultrasound catheter. The ultrasound sensing capabilities may for instance be provided by a plurality of transducer elements in a main surface of the ultrasonic transducer chip, e.g. to provide a forward looking or sideward looking ultrasound probe. Popular technologies to implement the transducer elements include piezoelectric transducer elements formed of materials such as lead zirconate titanate (PZT) or polyvinylidene-fluoride (PVDF) and capacitive micro-machined ultrasonic transducer (CMUT) elements. An ultrasonic transducer chip based on such CMUT elements is sometimes referred to as a CMUT device.

CMUT devices are becoming increasingly popular because CMUT devices can offer excellent bandwidth and acoustic impedance characteristics, which makes them the preferable over e.g. piezoelectric transducers. Vibration of the CMUT membrane can be triggered by applying pressure (for example using ultrasound) or can be induced electrically. Electrical connection to the CMUT device, often by means of an integrated circuit (IC) such as an application specific integrated circuit (ASIC) facilitates both transmission and reception modes of the device. In reception mode, changes in the membrane position cause changes in electrical capacitance, which can be registered electronically. In transmission mode, applying an electrical signal causes vibration of the membrane. A pressure causes a deflection of the membrane that is electronically sensed as a change of capacitance. A pressure reading can then be derived.

Miniaturization is a particular challenge when developing ultrasound probes. In particular, where such probes are to be used for advanced diagnostic purposes, e.g. cardiac investigations and surgery, such probes must be as small as possible to allow the probe to enter the body part of interest. At the same time, the ultrasound probe should be rigid, e.g. when used as the tip of a catheter to allow the probe to be guided into the body part of interest in a controlled manner. These requirements are difficult to reconcile with the desire to include significant signal processing capability at the probe.

Specifically, it may be desirable to include active components, e.g. application specific integrated circuits (ASICs) at the probe tip to provide the ultrasound transducer cells with control signals and to process the response signals, as well as passive components such as decoupling capacitors that for instance protect the various circuits from fluctuations in the supply voltage, e.g. supply bounce, which can be caused by the power consumption behaviour some of the components, in particular the ASICs.

US 2010/0280388 A1 discloses a CMUT array mounted on a flexible member together with support electronics. This subassembly can be rolled into a tube (cylinder) to form a CMUT based ultrasonic scanner, wherein ultrasound transducers are distributed over the side surface of said cylinder. However, it is not straightforward to achieve a sufficiently compact ultrasonic scanner in this manner. Specifically, in order to mount the subassembly onto a catheter lumen, the subassembly is typically connected to a printed circuit board (PCB) carrying further support electronics such as discrete components, e.g. decoupling capacitors, that cannot be readily formed in the subassembly manufacturing process, e.g. because these components are manufactured in a different technology. The PCB is connected to a number of coaxial wires inside the lumen, the number typically matching the number of channels of the ultrasonic scanner. Such a PCB gives the desired rigidity to the ultrasonic scanner. However, the minimum dimensions of the PCB and discrete components typically preclude sufficient miniaturization to facilitate use of such probes in dimensionally challenging environments, e.g. cardiac environments. Yet another disadvantage of the array shown is US 2010/0280388 A1 is its limited field of view in the forward looking direction.

SUMMARY OF THE INVENTION

The present invention seeks to provide an ultrasound transducer assembly that obviates the need for a separate PCB.

The present invention seeks to provide a coaxial wire assembly that can be connected to such an ultrasound transducer assembly in a straightforward manner.

The present invention further seeks to provide an ultrasound probe including such an ultrasound transducer assembly and coaxial wire assembly connected to each other.

The present invention yet further seeks to provide an ultrasonic imaging system including such an ultrasound probe.

According to an aspect, there is provided a foldable ultrasound transducer arrangement comprising a plurality of substrate islands spatially separated and electrically interconnected by a flexible polymer assembly including electrically conductive tracks providing said electrical interconnections, said plurality including a first substrate island comprising a plurality of ultrasound transducer cells and a second substrate island comprising an array of external contacts for connecting the ultrasound sensor arrangement to a flexible tubular body; and a rigid support structure having a first planar portion comprising a first surface, a second planar portion opposite the first portion having a second surface and a third planar portion having a third surface extending between the first surface and the second surface, wherein the foldable ultrasound transducer arrangement is arranged to be folded onto the support structure such that the first substrate island is mounted on the first surface and the second island is mounted on the second surface.

The present invention is based on the insight that some embodiments of a flexible transducer arrangement may be provided that can be folded onto a pre-shaped rigid carrier (structure) such that the transducer arrangement can be directly connected to a set of coaxial wires without requirement of an interconnecting PCB. Consequently, a particularly compact transducer assembly may be produced that can be used in an ultrasound probe for a flexible tubular body such as a catheter. In addition the first substrate island comprising a plurality of ultrasound transducer cells may provide a high density ultrasound array capable of acquiring high resolution ultrasound images in a forward looking direction away from the first surface of the rigid support structure.

Advantageously, the ultrasound transducer assembly further comprises at least one further substrate island comprising a plurality of external contacts for receiving active and/or passive components. This further obviates the need for a separate PCB as the further substrate islands can act as mounting pads for such active components, e.g. ASICs, and/or passive components, e.g. decoupling capacitors.

In an embodiment, at least one of the first substrate island, the second substrate island and the at least one further substrate island comprises a plurality of trenches defining a decoupling capacitor, each trench being filled by a conductive material separated from the substrate material by an electrically insulating material. Such an embedded vertical or trench capacitor may have a large plate area due to the three-dimensional nature of such a capacitor and may therefore function as a decoupling capacitor, thus obviating the need for discrete capacitors. This further reduces the overall size of the ultrasound transducer arrangement as discrete decoupling capacitors are typically relatively large and in some application domains are too large to facilitate sufficient miniaturization of the ultrasound transducer arrangement.

The ultrasound transducer arrangement may comprise a plurality of said decoupling capacitors, each decoupling capacitor being located on a different substrate island. This has the further advantage that the respective decoupling capacitors are truly electrically insulated from each other, such that different decoupling capacitors may be operated at different potentials, i.e. the substrates may be operated at different potentials. This increases the operational flexibility and robustness of the ultrasound transducer arrangement.

In an alternative embodiment, the flexible polymer assembly is a strip-shaped assembly and the first substrate island and the second substrate island are at opposite ends of the strip-shaped assembly, the ultrasound transducer arrangement further comprising a plurality of support islands in between the first substrate island and the second substrate island, the respective substrate and support islands being interconnected by the flexible polymer assembly.

This allows for the formation of a compact rigid ultrasound transducer assembly in which the need for a separate PCB or pre-shaped rigid carrier can be avoided.

The ultrasound transducer arrangement may further comprise at least one further substrate island comprising a plurality of external contacts for receiving active and/or passive components, said at least one further substrate island being mounted on the third planar portion. Due to the planar nature of the second surface in between the first surface and the third surface, such components can be added to the ultrasound transducer arrangement whilst retaining a compact arrangement. The ultrasound transducer may include active and/or passive components mounted on the at least one further substrate island.

The rigid support structure may be a metal support structure. This provides a particularly rigid support structure than can be manufactured at low cost.

The first substrate island may be separated from the first surface by a backing member in order to insulate the ultrasound transducer cells from scattered ultrasound waves from undesirable directions.

According to another aspect, there is provided an ultrasound transducer assembly comprising a backing member; and the ultrasound transducer arrangement according to the alternative embodiment, wherein the first substrate island is mounted on a first surface of the backing member and said strip-shaped assembly is folded to define a plurality of meandering folds mounted on a second surface of the backing member opposite said first surface, wherein the folds are dimensioned such that neighbouring support islands are adhered together within a single fold, and wherein the second substrate island is exposed at a distal end of the folded strip-shaped assembly relative to the backing member. This provides a compact and rigid ultrasound transducer assembly without requiring a separate rigid support structure.

According to yet another aspect, there is provided a coaxial wire assembly comprising a plurality of coaxial wires each having a conductive core covered by an electrically insulating sleeve; and a electrically insulating body having a first main surface, a second main surface and a plurality of through holes each extending from the first main surface to the second main surface, each of said holes being coated with an electrically conductive member; wherein each coaxial wire comprises an exposed terminal core portion mounted in one of said though holes from the first main surface, and wherein each through hole is sealed by a solder bump on the second main surface.

By securing the coaxial wires in a connection pad, which may for instance act as a ball grid array, a connection between the coaxial wires and the item to be connected thereto, e.g. the second substrate island of the ultrasound transducer arrangement, can be made in a simple and straightforward manner. To this end, the coaxial wire assembly may further comprise a flexible tubular body such as a catheter lumen housing said coaxial wires, wherein the electrically insulating body is mounted on an end portion of the flexible tubular body. However, it should be understood that such a coaxial wire assembly is not limited to connecting with the coaxial wire assembly of the present invention; such a coaxial wire assembly may be connected to any item that requires connection to a plurality of coaxial wires. Specifically, the coaxial wire assembly may be connected to an edge portion of a carrier such as a PCB to facilitate a straightforward connection between the coaxial wire assembly and the carrier.

According to a further aspect, there is provided an ultrasound probe comprising one or more embodiments of the above ultrasound transducer assembly and the coaxial wire assembly, wherein each of the external contacts of the second substrate island is conductively coupled to one of the solder bumps. This yields a particularly compact and rigid ultrasound probe that can be reliably used in small spaces such as cardiac volumes.

According to a yet further aspect, there is provided an ultrasonic imaging system including such an ultrasound probe. Such an imaging system can be reliably used to produce images of small spaces of interest, such as cardiac volumes.

BRIEF DESCRIPTION OF THE DRAWINGS

Embodiments of the invention are described in more detail and by way of non-limiting examples with reference to the accompanying drawings, wherein.

DETAILED DESCRIPTION OF THE EMBODIMENTS

Figure 1:
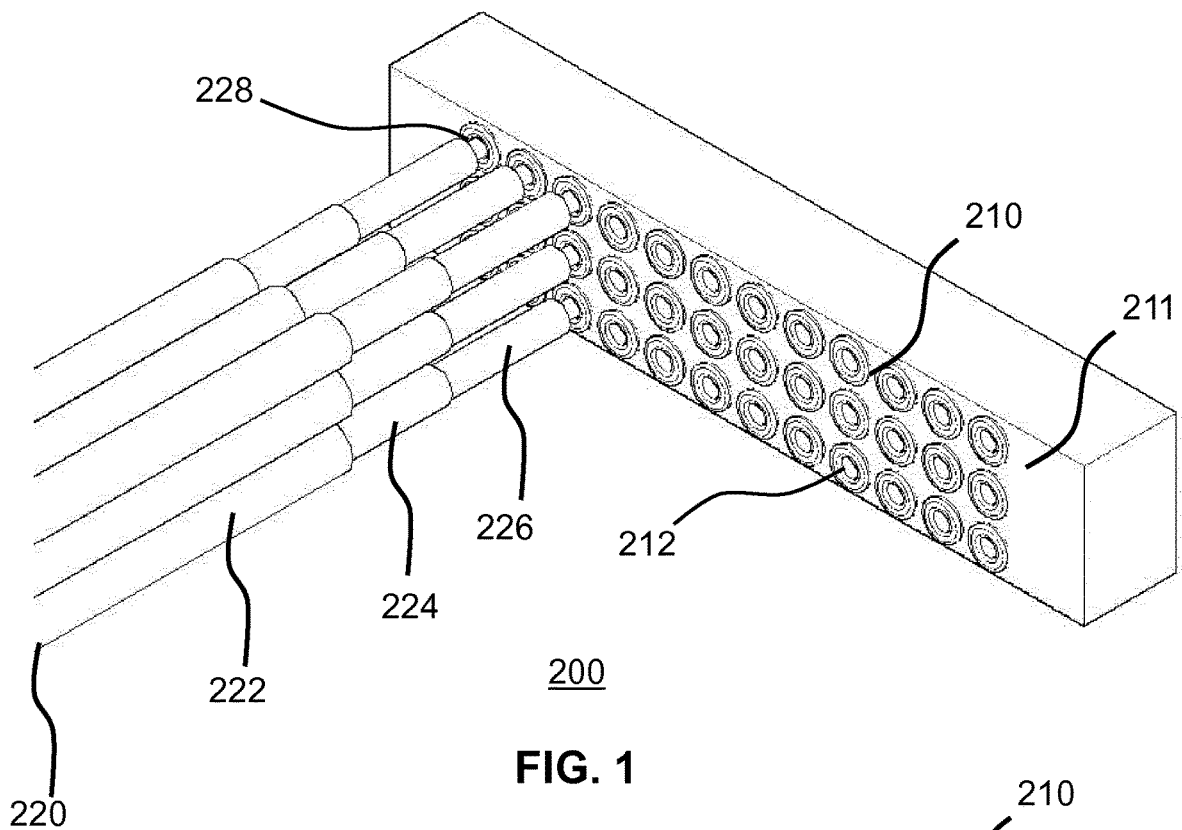
FIG. 1 schematically depicts an aspect of a coaxial wire assembly according to an embodiment.

It should be understood that the Figures are merely schematic and are not drawn to scale. It should also be understood that the same reference numerals are used throughout the Figures to indicate the same or similar parts.

Embodiments of the present invention are directed to the provision of a compact and rigid ultrasound probe tip where the rigidity of the tip can be provided without the need for a printed circuit board (PCB). To this end, a plug and socket type arrangement has been devised in which an ultrasound transducer assembly and a coaxial wire assembly are directly mated to connect the ultrasound transducer assembly to a flexible lumen such as a flexible catheter, in contrast to prior art arrangements in which the ultrasound transducer assembly is typically mounted to a PCB onto which the coaxial wires are soldered. As previously explained, these prior art arrangements cannot achieve the desired miniaturization of the ultrasound probe tip due to the size constraints of the PCB.

Figure 2:
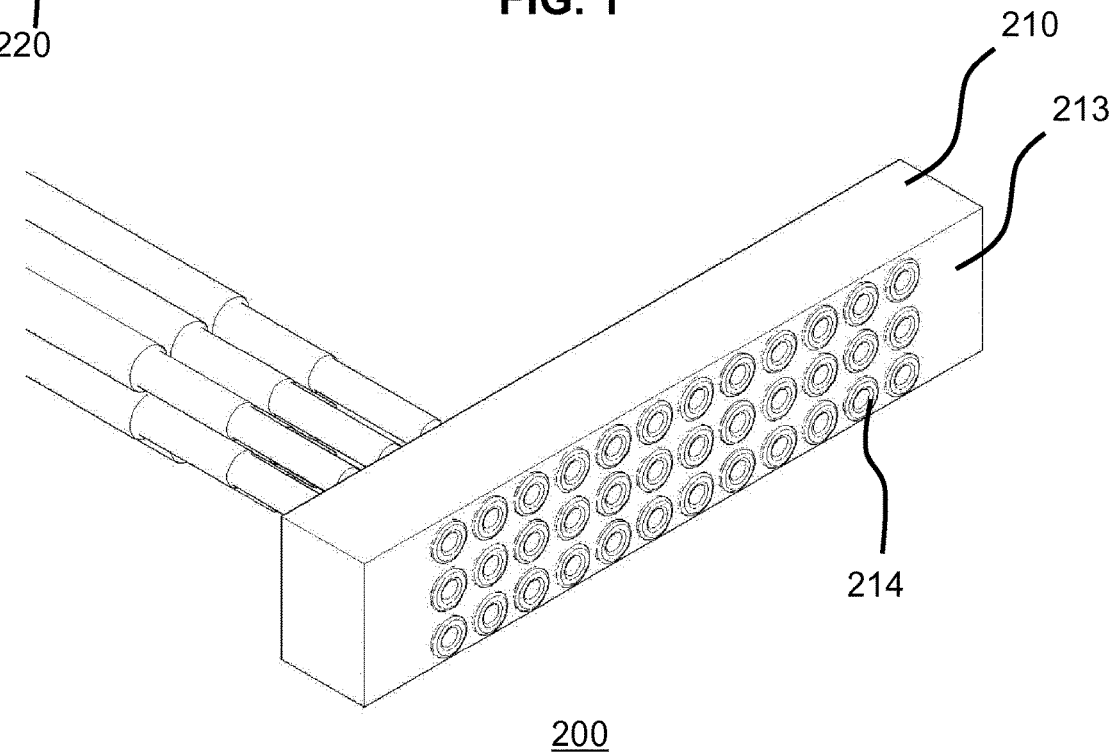
FIG. 2 schematically depicts another aspect of a coaxial wire assembly according to an embodiment.

FIGS. 1 and 2 schematically provide respective perspective views of a coaxial wire assembly 200 according to an embodiment. The coaxial wire assembly 200 comprises a plurality of coaxial wires 220 each having a conductive core 228 covered by an electrically insulating sleeve 226. The electrically insulating sleeve 226 typically separates the electrically conductive core 228 from an electrically conductive outer sheath 224, which is electrically insulated by an outer sleeve 222. As such coaxial wires 220 are well known per se, this will not be explained in further detail. It is however noted for the avoidance of doubt that any suitable type of coaxial wire may be used in the coaxial wire assembly 200.

The coaxial wire assembly further comprises an electrically insulating body 210 having a first main surface 211, a second main surface 213 and a plurality of through holes 212 each extending from the first main surface 211 to the second main surface 213. Each of said through holes 212 is coated with an electrically conductive member, e.g. a metal or metal alloy layer which may be applied to the inner surface of the through holes 212 in any suitable manner, e.g. by any suitable plating technique. The through holes 212 may be formed in the electrically insulating body 210 in any suitable manner, for instance using a suitable etch recipe. The electrically insulating body 210 may be made of any suitable material, such as for instance undoped silicon or any other electrically insulating material through which the through holes 212 may be formed in a suitable manner, e.g. any electrically insulating material that can be etched to form the through holes 212. Each coaxial wire 220 comprises an exposed terminal core portion where the electrically insulating sleeve 226 has been stripped back to expose the terminal core portion. Each exposed terminal core portion is mounted in one of the though holes 212 such that the terminal core portion enters the through hole 212 from the first main surface 211. Each terminal core portion is secured in its through hole 212 such that the terminal core portion is electrically coupled to the electrically conductive member inside the through hole 212. For instance, the terminal core portion may be secured in the through hole 212 using a solder. Each through hole 212 may be further sealed by a solder bump (not shown) on the second main surface 213, which solder bumps may define a ball grid array on the second main surface 213. The solder bump may form part of the solder securing the terminal core portion inside the through hole 212. Alternatively, the electrically conductive member formed inside each through hole 212 may be shaped such that the electrically conductive members protrude from the second main surface 213, which protrusions may instead define an array of contacts on the second main surface 213. In an embodiment, the coaxial wires 220 form part of a flexible lumen such as a catheter, wherein the coaxial wires 220 are typically housed within a flexible tubular body as is well known per se. In this embodiment, the array of contacts, e.g. a ball grid array, may be used to directly connect the flexible lumen to an ultrasound transducer assembly, i.e. without the need to connect the coaxial wires 220 to a PCB, as will be explained in more detail later.

However, it should be understood that the coaxial wire assembly 200 is not limited to such a use. The coaxial wire assembly 200 may be used as a coaxial wire connection to any further assembly that requires a plurality of coaxial wires to be connected thereto. In particular, the coaxial wire assembly 200 may be advantageously used in devices in which the coaxial wires 220 are to be connected in relatively close vicinity to each other, where the required close vicinity makes it difficult to reliably establish the desired interconnections on an individual basis. For instance, the coaxial wire assembly 200 according to embodiments can facilitate a connection matrix of coaxial wires 220 having a pitch of 200 microns or less.

Figure 3:
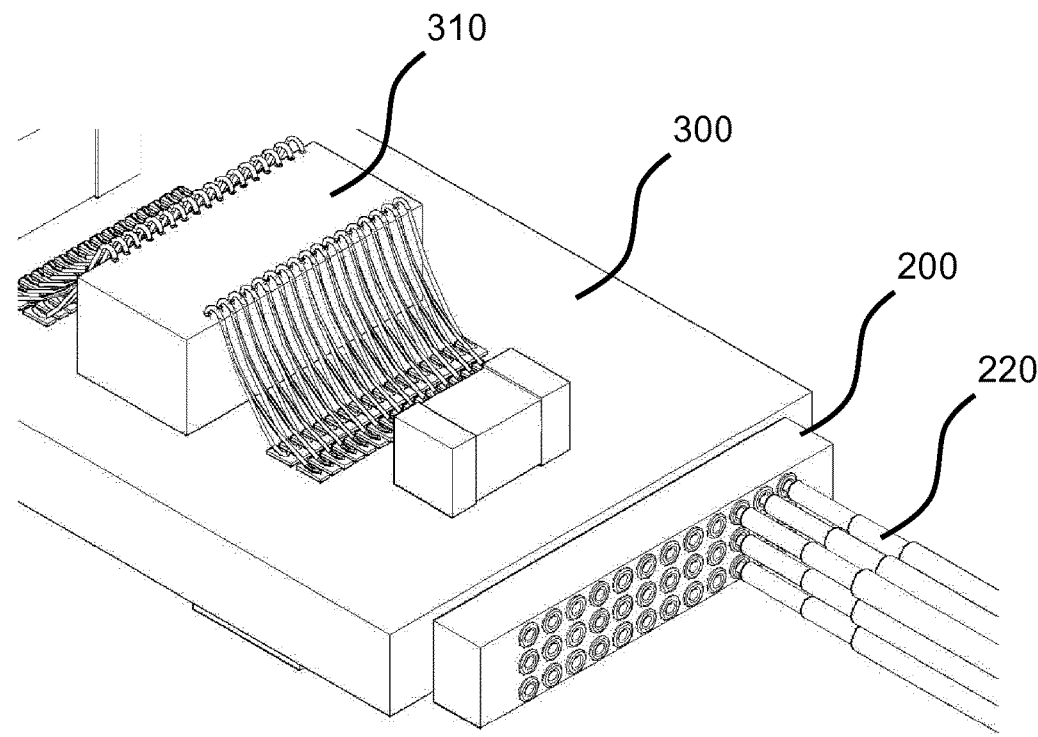
FIG. 3 schematically depicts a coaxial wire assembly according to an embodiment mounted onto an edge of a printed circuit board.

FIG. 3 schematically depicts an example in which the coaxial wire assembly 200 is mounted to a PCB 300 carrying one or more discrete components 310. Here, the coaxial wire assembly 200 is electrically coupled, e.g. soldered or glued using drops of a conductive glue between opposing contacts, to an edge portion of the PCB 300. Such an edge arrangement is particularly compact and may be achieved because the coaxial wire assembly 200 may have an overall height of about 1 mm or less, which is well within the thickness of most PCBs. More generally, the form factor of the coaxial wire assembly 200 makes it particular suitable for connection to an edge portion of a further assembly, where the edge portion connects two opposing major surfaces of the further assembly.

In a specific embodiment, the coaxial wire assembly 200 may form part of a flexible lumen, e.g. a catheter, and may be used to form a compact rigid probe tip with an ultrasound transducer arrangement, where the ultrasound transducer arrangement is designed to comprise a substrate island comprising an array of external contacts for connecting the ultrasound sensor arrangement to the catheter via the coaxial wire assembly 200 without the need for an intermediary rigid carrier such as a PCB in between the ultrasound transducer arrangement and the coaxial wire assembly 200.

Figure 4:
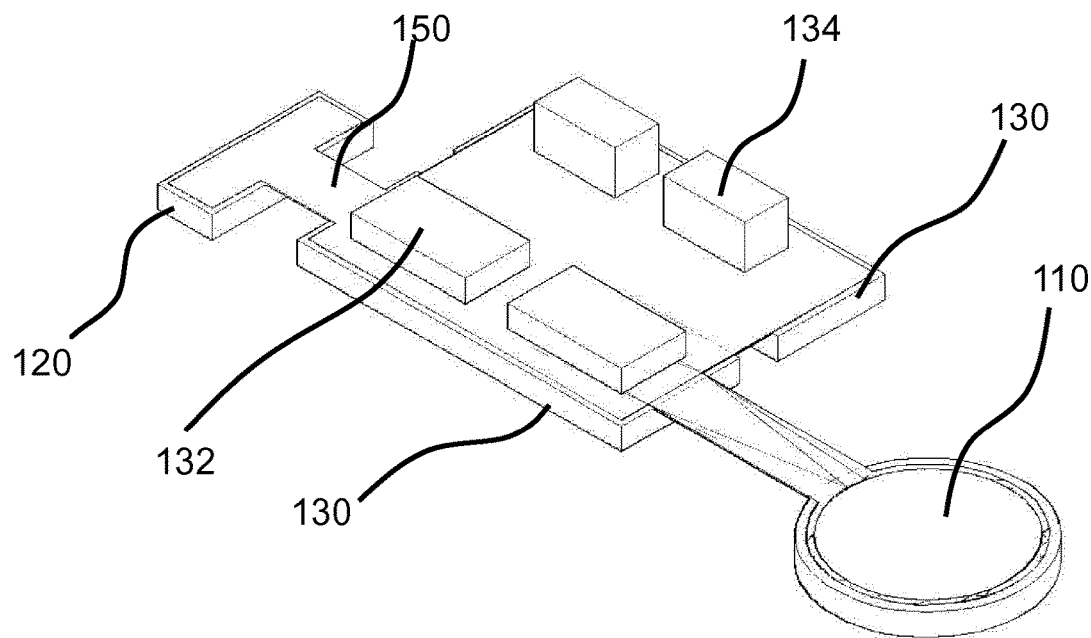
FIG. 4 schematically depicts an ultrasound transducer arrangement according to an embodiment.

FIG. 4 schematically depicts an ultrasound transducer arrangement 100 according to such an embodiment. The ultrasound transducer arrangement 100 typically comprises an ultrasonic transducer substrate island or chip 110 having a major surface comprising an ultrasound transducer area, which typically comprises a plurality of transducer elements, such as CMUT or PZT elements. In a preferred embodiment, the major surface comprises an ultrasound transducer area formed by a plurality of CMUT elements.

The major surface further comprises a plurality of contacts, which may provide points of contact to the transducer elements in any suitable manner as is well-known per se. Any suitable embodiment of such a transducer substrate island or chip 110 may be chosen; it should be understood that embodiments of the present invention are not limited to a particular embodiment of such a transducer chip. For instance, the transducer chip 110 may be realized in any suitable semiconductor technology, e.g. CMOS, BiCMOS, bipolar technology and so on, using any suitable semiconductor substrate material, e.g. silicon, silicon-on-insulator, SiGe, GaAs and so on. Moreover, it should be understood that the transducer substrate island or chip 110 is shown as a circular chip by way of non-limiting example only; the transducer substrate island or chip 110 may take any suitable shape or form.

The ultrasonic transducer assembly further comprises a contact substrate island or chip 120 spatially separated from the transducer substrate island or chip 110 by a flexible polymer assembly 150 including, e.g., embedding, conductive tracks between the transducer substrate island or chip 110 and the contact substrate island or chip 120. The contact chip 120 typically comprises a plurality of external contacts 420 for engaging with the coaxial wire assembly 200 as will be explained in more detail later. Any suitable embodiment of such a contact substrate island or chip 120 may be chosen; it should be understood that embodiments of the present invention are not limited to a particular embodiment of such a contact chip. For instance, the contact chip 120 may be realized in any suitable semiconductor technology, e.g. CMOS, BiCMOS, bipolar technology and so on, using any suitable semiconductor substrate material, e.g. silicon, silicon-on-insulator, SiGe, GaAs and so on.

The external contacts may be realized in any suitable electrically conductive material, such as any material that is commonly used for the formation of such contacts, e.g. any suitable metal or metal alloy. In an embodiment, the external contacts 420 carry a solder bump for establishing the electrical connection with the coaxial wire assembly 200.

The flexible polymer assembly 150 may for instance be formed of an electrically insulating flexible polymer such as polyimide, wherein the conductive tracks may be formed by depositing a metal layer such as a copper layer over the electrically insulating flexible polymer and patterning the metal layer to form the conductive tracks. In an embodiment, the flexible interconnect 150 may be a Flex foil or a copper-coated polyimide such as a Pyralux® foil as marketed by the Du Pont company.

In the embodiment shown in FIG. 4, the ultrasonic transducer substrate island or chip 110 and the contact substrate island or chip 120 may be discretely manufactured chips, e.g. chips manufactured in different manufacturing processes using different technologies, which chips are interconnected to each other by the flexible polymer assembly 150 after singulation. This has the advantage of increased flexibility in the designs of the ultrasonic transducer chips 110 and the contact chips 120, but comes at the cost of a more involved assembly process of the ultrasonic producer assembly, as it can be cumbersome to connect the flexible interconnect 150 to the respective chips 110, 120. Therefore, in an alternative embodiment, which will be explained in more detail later with the aid of FIG. 9, the ultrasonic transducer substrate island or chip 110, the contact substrate island or chip 120 and the flexible polymer assembly 150 may be produced in a single (integrated) production process.

The ultrasound transducer arrangement 100 may further comprise one or more mounting substrate islands or chips 130, which may be realized in the same technology as the ultrasonic transducer substrate island or chip 110 and/or the contact substrate island or chip 120, i.e. in a single integrated production process, or in a distinct technology as previously explained. The one or more mounting substrate islands or chips 130 are electrically connected to the ultrasonic transducer substrate island or chip 110 and/or the contact substrate island or chip 120 through the conductive tracks in the flexible polymer assembly 150. The one or more mounting substrate islands or chips 130 comprise contacts on an exposed surface onto which active components 132, e.g. transducer controllers and/or signal processing components such as ICs, e.g. application-specific ICs (ASICs), or passive components 134, e.g. decoupling capacitors or the like, may be mounted in any suitable manner, e.g. soldered, thermo compression bonded, and so on. This has the advantage that discrete components may be added to the ultrasound transducer arrangement 100 without having to manufacture these components in the same technology as for instance the ultrasonic transducer substrate island or chip 110. This increases the design flexibility of the ultrasound transducer arrangement 100. The at least one mounting substrate island or chip 130 in essence serves as a replacement mounting platform for such discrete components, thereby facilitating the omission of a PCB from an ultrasound transducer assembly including the ultrasound transducer arrangement 100.

It should however be understood that embodiments the present invention are not limited to such discrete components being mounted on dedicated substrate islands 130; it is equally feasible that the ultrasonic transducer substrate island or chip 110 and/or the contact substrate island or chip 120 contain such external contacts for mounting such discrete components in addition to or instead of on the mounting substrate islands or chips 130.

Figure 5:
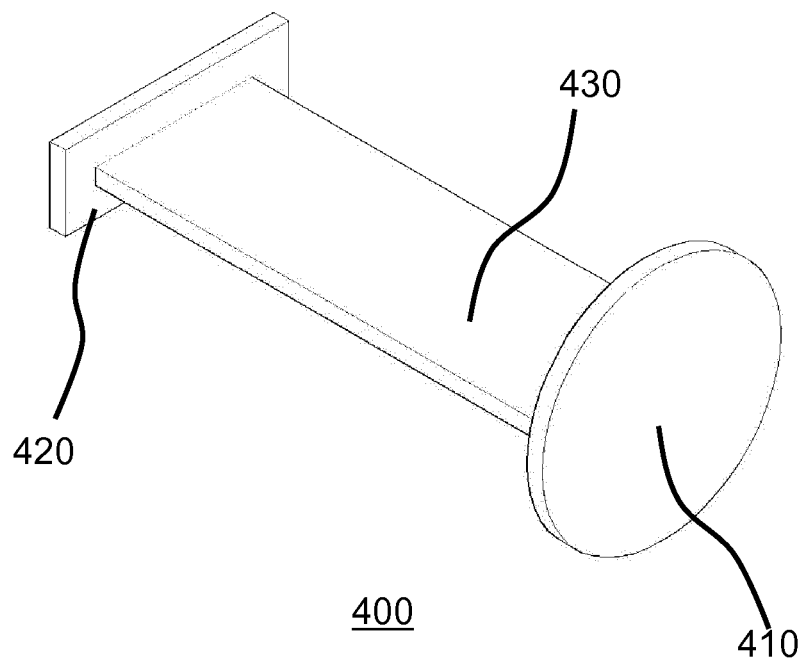
FIG. 5 schematically depicts a rigid carrier onto which the ultrasound transducer arrangement of FIG. 4 can be mounted.
Figure 6:
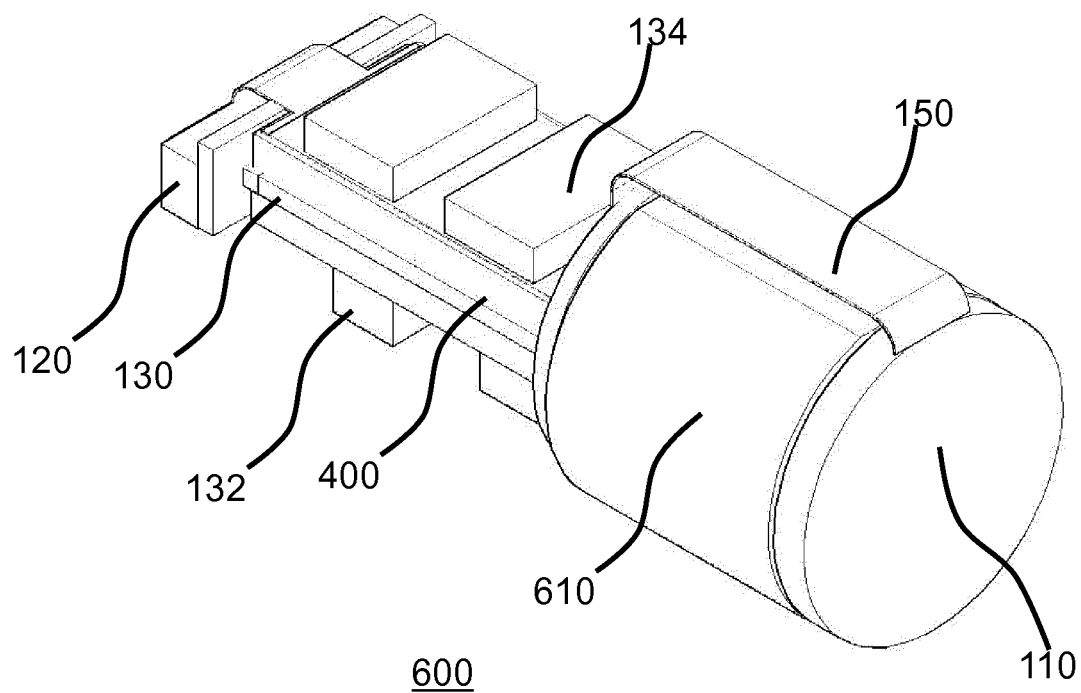
FIG. 6 schematically depicts an ultrasound transducer assembly according to an embodiment.

In the absence of such a PCB, additional measures are required to ensure that the ultrasound transducer assembly achieves the desired stiffness when used as a probe tip of e.g. an invasive diagnostic device such as a catheter. In a first embodiment, the ultrasound transducer arrangement 100 may be mounted on a pre-shaped rigid support structure 400, an example embodiment of which is schematically depicted in FIG. 5 to form an ultrasound transducer assembly 600 as schematically depicted in FIG. 6. The rigid support structure 400 may have a first planar portion 410 comprising a first surface for supporting the ultrasonic transducer substrate island or chip 110, a second planar portion 420 opposite the first portion 410 having a second surface for supporting the contact substrate island or chip 120 and a third planar portion 430 having a third surface extending between the first surface and the second surface for supporting the one or more mounting substrate islands or chips 130, which one or more mounting substrate islands or chips 130 may carry active components 132 and/or passive components 134 as previously explained. The third planar portion may be aligned with an overall length of a probe (while being perpendicular to the first and second surfaces), wherein such an assembly can be used. In an embodiment, both main surfaces of the third planar portion 430 may be used to support mounting substrate islands or chips 130.

The ultrasound transducer arrangement 100 may be mounted on the rigid support 400 by folding the flexible polymer assembly 150 such that the relevant substrate islands are mounted on the aforementioned planar surfaces. To this end, the flexible polymer assembly 150 may be shaped, e.g. patterned, to contain multiple flaps each carrying one or more of the substrate islands, which flaps are folded over the appropriate planar surface of the rigid support structure 400 to form the rigid ultrasound transducer assembly 600. The ultrasound transducer arrangement 100 may be secured on the rigid support structure 400 in any suitable manner, e.g. using a suitable adhesive, which will be known per se to the person skilled in the art.

The rigid support structure 400 may be made of any suitable rigid material, such as a rigid (bio)polymer, a metal, metal alloy, e.g. stainless steel, and so on. In an embodiment, the rigid support structure 400 is made of a rigid material that is cleared for internal use in a patient, e.g. titanium or stainless steel. The rigid support structure 400 may take any suitable shape. In an embodiment, the first surface of the first planar portion 410 is substantially parallel with the second surface of the second planar portion 420, wherein the first surface and second surface face opposite directions.

This for instance may be used to provide an ultrasound transducer assembly 600 having a forward looking ultrasound transducer array and a contact substrate island or chip 120 being arranged to connect to a coaxial wire assembly 100 mounted on a tip of a flexible tubular member, e.g. a lumen or catheter. Upon connection of such a ultrasound transducer assembly 600 to such a coaxial wire assembly 100, a particularly compact probe tip can be achieved, e.g. having the overall length from transducer chip 110 to contact chip 120 of less than 10 mm, or even less than 8 mm, with a high degree of rigidity, thus providing an ultrasound probe tip that is particularly suitable for investigations and procedures involving small body volumes, e.g. cardiac investigations and procedures. The advantage of such a probe comprising the forward looking ultrasound array located at its tip's front surface may be compact size and a capability of high resolution ultrasound imaging due to the possibility in varying the transducer density within ultrasonic transducer substrate island 110.

Optionally, in the ultrasound transducer assembly 600 used for the probe tip, the ultrasonic transducer chip 110 may be separated from the first surface of the first planar portion 410 by a backing member 610. In this embodiment, at least a part of the flexible polymer assembly 150 may extend along an outer side of the backing member 610, such that the transducer chip 110 and the contact ship 120 are electrically interconnected. The backing member 610 typically comprises a resin such as an epoxy resin in which ultrasound scattering and/or absorbing bodies are included. For instance, the ultrasound scattering bodies and/or ultrasound absorbing bodies may be dispersed in the resin. Such bodies suppress or even prevent scattered and/or reflected ultrasound waves from reaching the ultrasonic transducer elements of the ultrasonic transducer chip 110. This may improve the resolution of the ultrasound image generated by the ultrasonic transducer chip 110, as predominantly or only ultrasound waves generated and reflected in the intended direction (e.g. forward generated and reflected ultrasound waves in the case of a forward-looking ultrasound probe including the ultrasonic transducer chip 100) are detected by the ultrasonic transducer elements of the ultrasonic transducer chip 100. In other words, the suppression or prevention of ultrasound waves from other directions reaching the ultrasonic transducer chip 110 by the backing member 610 reduces or even avoids interference from such stray ultrasound waves with the ultrasound waves from the direction of interest.

Any suitable ultrasound scattering materials may be used to form the ultrasound scattering bodies in the backing member 610. For instance, a non-limiting example of such an ultrasound scattering body is a hollow glass sphere although other suitable ultrasound scattering bodies will be immediately apparent to the skilled person. Similarly, any suitable solid materials may be used to form the ultrasound absorbing bodies. It is well-known per se that heavy materials, e.g. materials based on heavy metals, are ideally suited for such a purpose. A non-limiting example of such a material is tungsten. For instance, the ultrasound absorbing bodies may comprise tungsten, such as in the form of tungsten oxide. Again, it will be immediately apparent to the skilled person that many suitable alternatives to tungsten are readily available, and such suitable alternatives are equally feasible to be used in the backing member 610.

Figure 7:
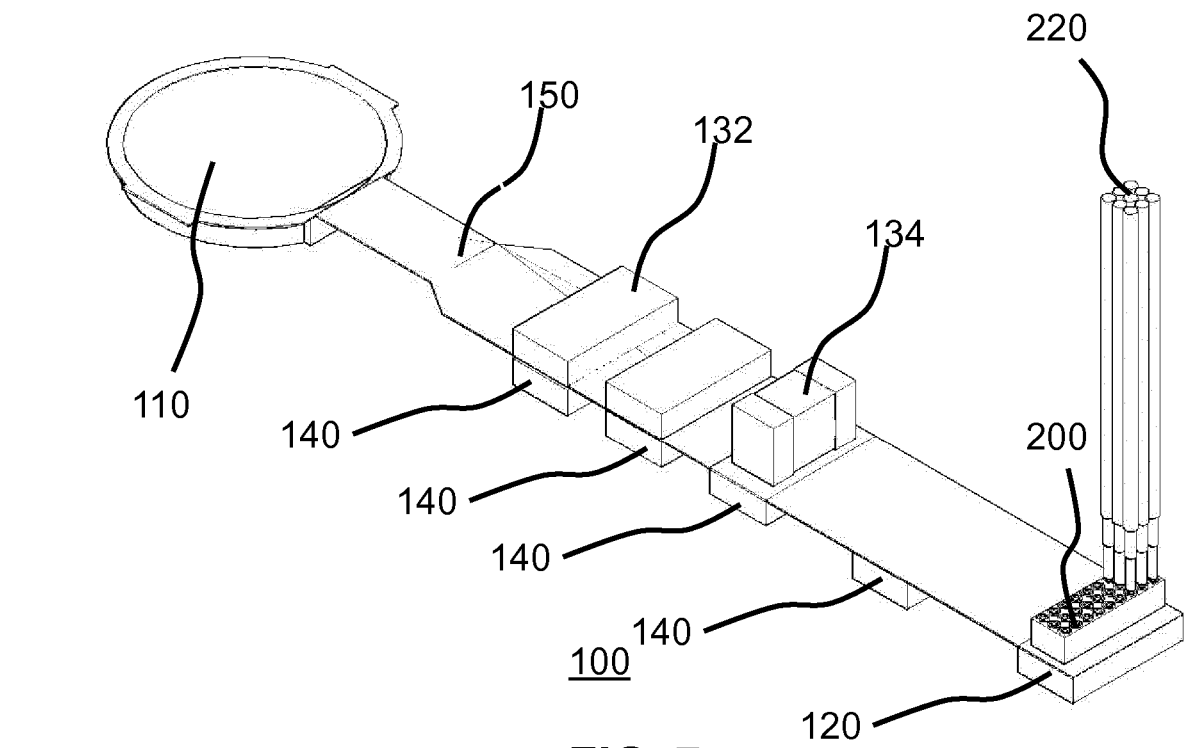
FIG. 7 schematically depicts an aspect of an ultrasound probe tip including an ultrasound transducer arrangement according to another embodiment.
Figure 8:
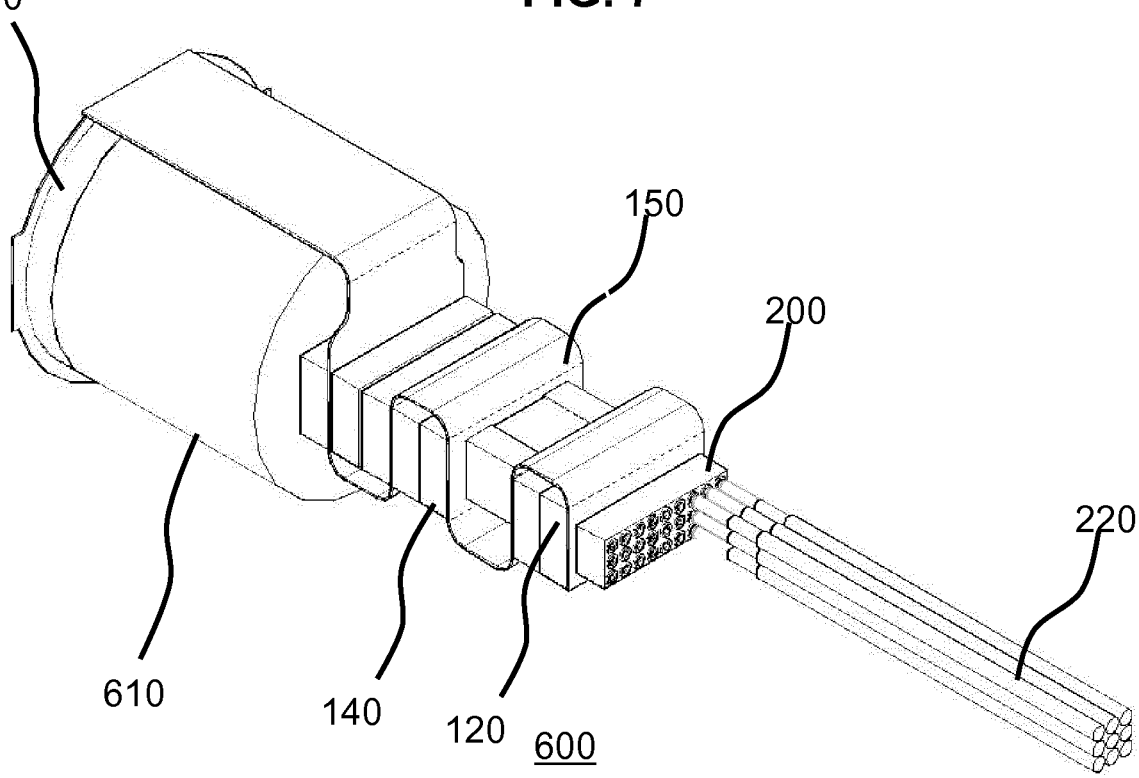
FIG. 8 schematically depicts the ultrasound probe tip of FIG. 7 with the ultrasound transducer arrangement in a folded arrangement.

FIG. 7 schematically depicts an alternative embodiment of an ultrasound transducer arrangement 100 that can be folded into a rigid ultrasound transducer assembly 600 having a plurality of meandering folds as schematically shown in FIG. 8. In this embodiment, the flexible polymer assembly 150 is shaped as an elongated strip, wherein the ultrasound transducer arrangement 100 in addition to the ultrasonic transducer substrate island or chip 110 and the contact substrate island or chip 120 further comprises a plurality of support substrate islands or chips 140 interconnected by the flexible polymer assembly 150 as previously explained.

The support substrate islands or chips 140 are spaced apart such that exposed major surfaces of neighbouring support substrate islands or chips 140 may be contacting each other when the flexible polymer assembly 150 is folded into a plurality of meandering loops or folds, with the neighbouring support substrate islands or chips 140 occupying a single fold or loop as shown in FIG. 8. The neighbouring support substrate islands or chips 140 may be secured to each other in any suitable manner, e.g. using a suitable adhesive. The support substrate islands or chips 140 act as rigid support members of the ultrasound transducer assembly 600 that help to give the ultrasound transducer assembly 600 its desired rigidity.

In an embodiment, at least some of the support substrate islands or chips 140 may perform the role of the previously described mounting substrate islands or chips 130. In other words, at least some of the support substrate islands or chips 140 may comprise contacts on an exposed surface onto which active components 132, e.g. transducer controllers and/or signal processing components such as ICs, e.g. application-specific ICs (ASICs), or passive components 134, e.g. decoupling capacitors or the like, may be mounted in any suitable manner, e.g. soldered, thermo compression bonded, and so on.

In an embodiment, the ultrasound transducer substrate island or chip 110 is spatially separated from a further substrate island, e.g. one of the support substrate islands or chips 140, by a backing member 610, which may be a backing member as previously explained. The ultrasound transducer substrate island or chip 110 and the further substrate island may be affixed to the backing member 610 in any suitable manner, e.g. using an adhesive.

The ultrasound transducer substrate island or chip 110 may be located at a proximal end and the contact substrate island or chip 120 may be located at a distal end of the strip-shaped flexible polymer assembly 150 relative to the backing member 610. As shown in FIG. 8, the contact substrate island or chip 120 may be connected to a coaxial wire assembly 200 comprising a plurality of coaxial wires 220 as previously discussed.

Figure 9:
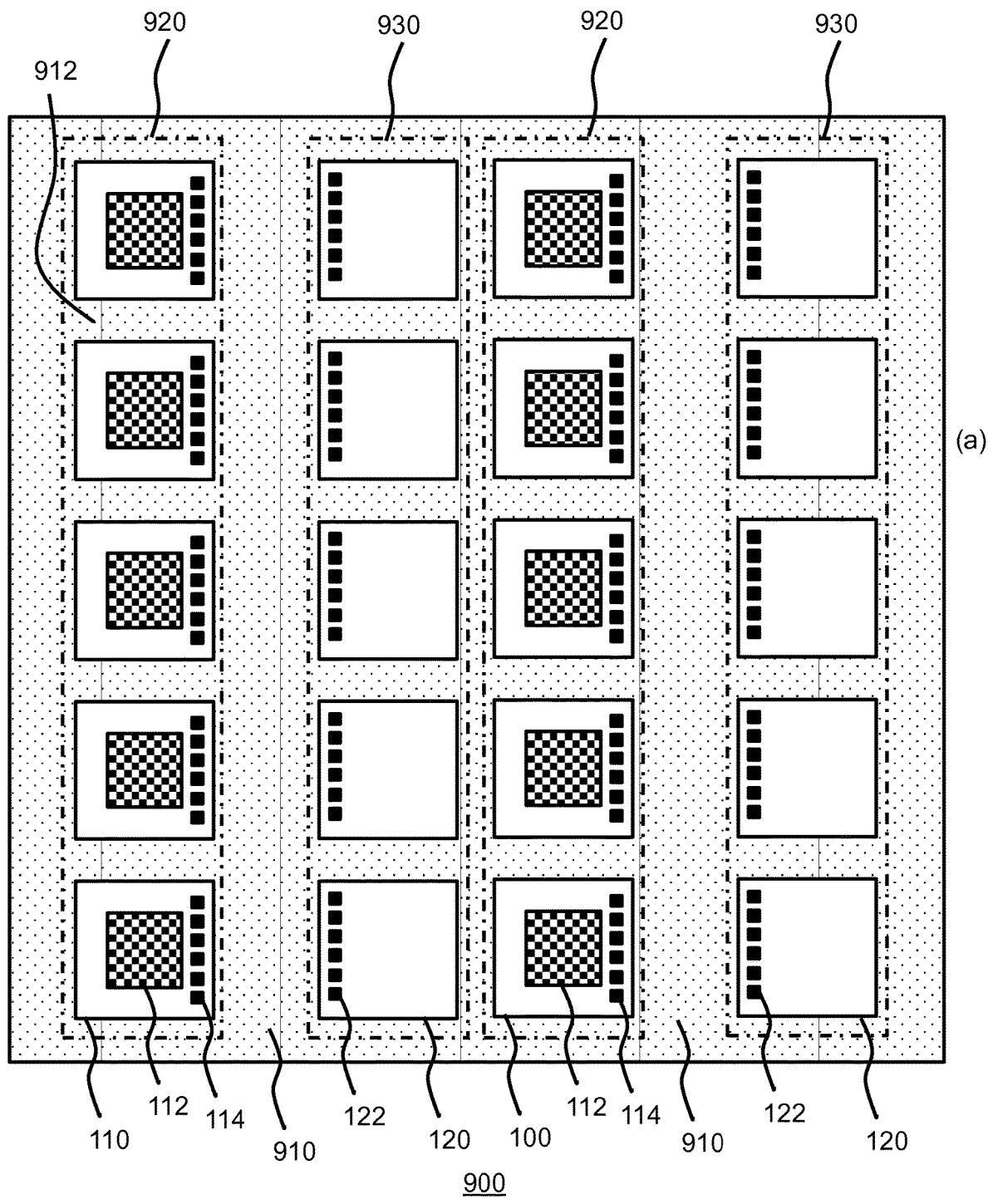
FIG. 9 schematically depicts an example embodiment of a method of manufacturing an ultrasound transducer arrangement.
Figure 9:
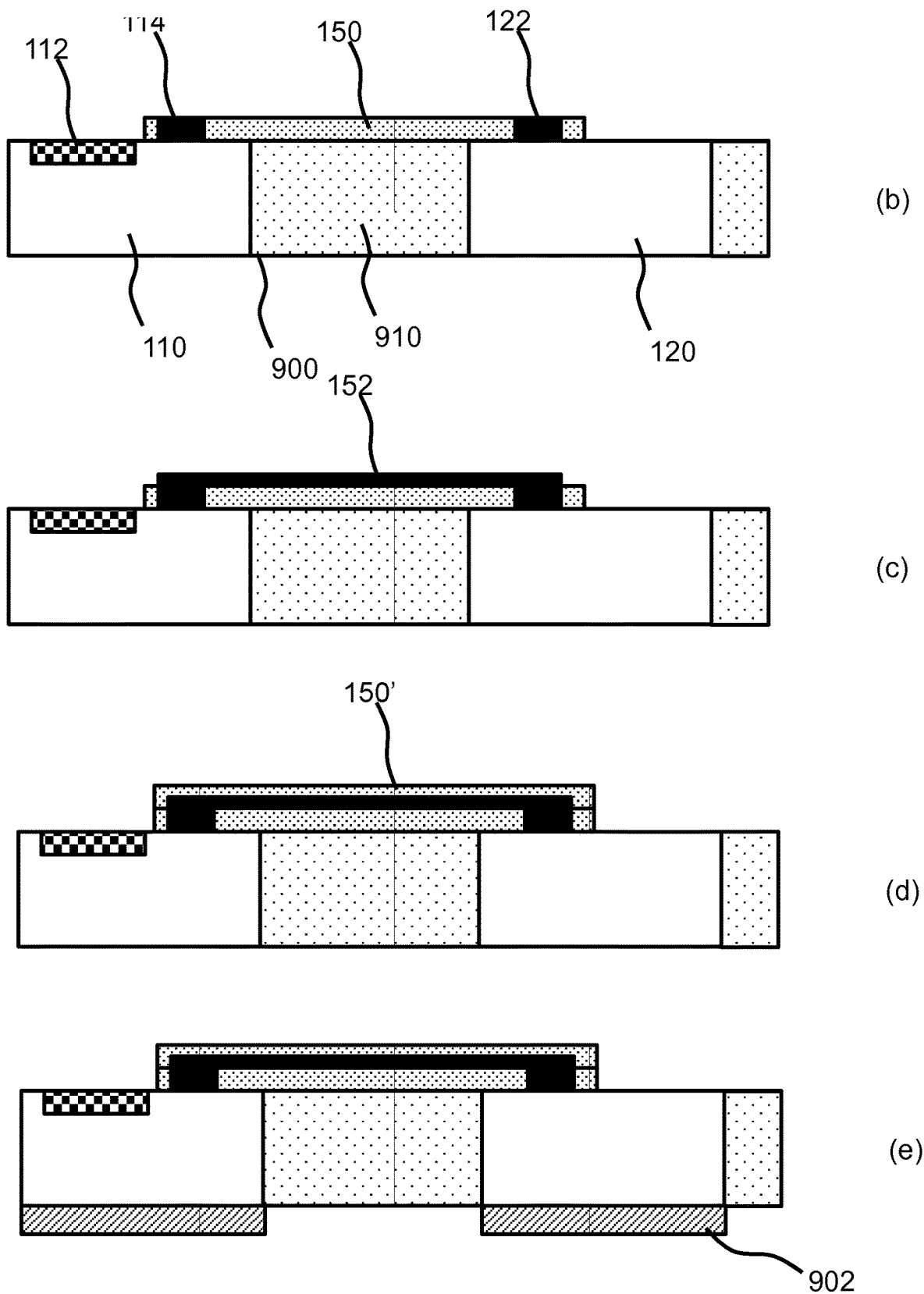
Figure 9:
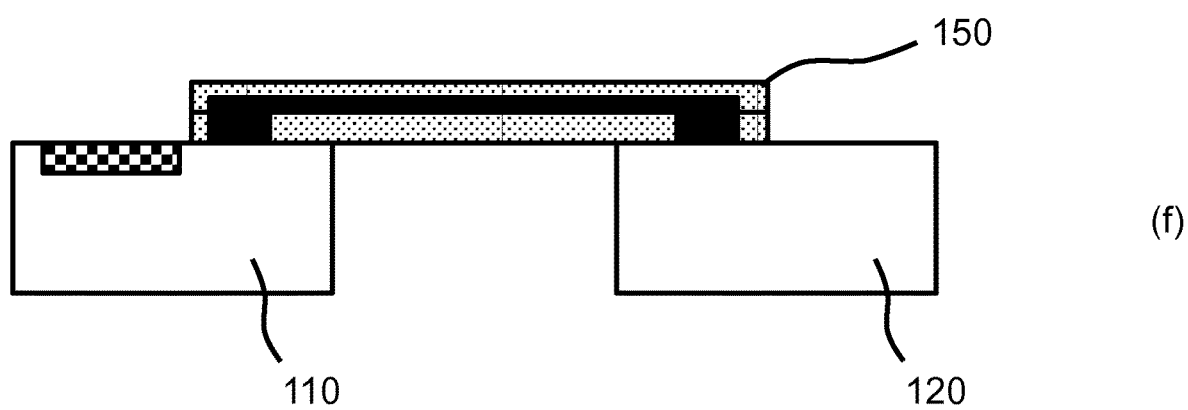

In FIG. 9, a non-limiting example of a method in accordance with an embodiment of the present invention is schematically depicted in which an ultrasound transducer arrangement 100 is formed. In a first step, depicted in FIG. 9(*a*), a wafer 900 is provided in which a plurality of ultrasonic transducer substrate islands or chips 110 having a plurality of ultrasonic transducer elements 112 and a plurality of first contacts 114 have been formed in one or more arrays 920 and in which contact substrate islands or chips 120 including a plurality of second contacts 122 are formed in one or more arrays 930 (two arrays 920, 930 are shown by way of non-limiting example). The arrays 920 of the ultrasonic transducer substrate islands or chips 110 are separated from a neighbouring array 930 of the contact substrate islands or chips 120 by a sacrificial region 910 of the wafer 900. Individual substrate islands or chips within each of the arrays 920, 930 are separated by a further sacrificial wafer region 912, e.g. a scribe line or the like as will be explained in more detail later.

The wafer 900 may be any suitable wafer, such as a silicon wafer, a silicon-on-insulator wafer or a wafer of other suitable semiconductor materials. In an embodiment, the wafer 900 may comprise an etch stop layer (not shown), such as an oxide layer. Its purpose will be explained in more detail later. The first contacts 114 of each ultrasonic transducer substrate island or chip 110 are to be connected to the second contacts 122 of an opposing contact substrate island or chip 120 by a flexible polymer assembly 150 extending across the sacrificial region 910. Such a flexible contact extension can be seen as a microscopic version of a flat cable, which use is well-known at the printed circuit board (PCB) level.

The method proceeds as shown in FIG. 9(*b*) with the provision of a layer of a flexible and electrically insulating material 150 on the front side of the wafer 900, which is subsequently patterned by photolithography to expose the first and second contacts 114, 122 underneath the layer 200. Any suitable material may be used for the layer 200. The flexible and electrically insulating material may be chosen from the group consisting of parylene, polyimide, polyimide resins, polycarbonate, fluorocarbon, polysulphon, epoxide, phenol, melamine, polyester, and silicone resins or their co-polymers. Polyimide and parylene are particularly suitable when the IC is to be integrated into an invasive medical device as these materials have been cleared for use in invasive medical devices.

The thickness of the layer of a flexible and electrically insulating material 150 preferably is selected in the range from 1-20 µm and more preferably in the range of 1-10 µm to ensure that the resultant has sufficient flexibility. If the layer 150 becomes too thick, its flexibility will be reduced. However, if the layer 150 becomes too thin, it may be damaged too easily.

In a subsequent step, shown in FIG. 9(*c*), a conductive material is deposited on the layer of the flexible and electrically insulating material 150 and subsequently patterned to provide respective conductive tracks 152 in conductive contact with the exposed first and second contacts 114, 122 underneath the layer 150. Any suitable electrically conductive material, such as Al, Cu or other suitable metals and metal alloys may be used.

In an optional step shown in FIG. 9(*d*), the conductive tracks 152 are subsequently covered with a second layer of a flexible and electrically insulating material 150', which preferably is the same material as used for layer 150, although this is not essential. In other words, the materials used for layers 150 and 150' respectively may be individually selected from the previously described group of suitable compounds.

In a preferred embodiment, layers 150 and 150' are made of the same material, e.g. polyimide or parylene, and have the same thickness, e.g. approximately 5 µm. By using the same thickness for both layers 150 and 150', the conductive track(s) 152 are situated at the so called neutral line of stress of the flexible contact extension of the contacts 114, 122. If present, the second layer 150' of a flexible and electrically insulating material may be covered with a thin protective layer (not shown) from subsequent wafer processing steps. Any suitable material, such as a metal, e.g. Al may be used. The use of a material that can serve both to protect the layer 150' during the subsequent processing steps as well as a hard-etch mask for the subsequent patterning of the second layer of a flexible and electrically insulating material 150' is preferred as it reduces the wafer processing complexity. For this reason, metals such as Al are preferred.

As shown in FIG. 9(*e*), the method proceeds by applying and patterning a resist layer 902 on the backside of the wafer 900. Alternatively the resist layer 902 may be replaced by a patterned hard mask. The patterned resist layer 902, which may be any suitable material including a similar or the same material used for the previously mentioned thin protective layer over the second layer 150', protects (covers) the areas of the arrays 920, 930 in the wafer 500.

In a final step, shown in FIG. 9(*f*), the exposed parts of the back-side of the wafer 900, i.e. the parts not covered by the patterned resist 902 are exposed to an etch recipe, preferably an anisotropic etch recipe such as the Bosch process, for instance in case of the wafer 900 being a silicon wafer, with the exposed parts being etched to a depth corresponding to the intended final thickness of the substrate islands or chips 110, 120 to be formed from the wafer 900, to release (singulate) the arrays 920, 930, with each array 920 connected to an array 530 by the flexible interconnect 200. It is noted that the Bosch process, which typically comprises consecutive etching and passivation steps, is well-known per se, and will therefore not be explained in further detail for reasons of brevity only. Other suitable etch recipes of course may also be contemplated. The patterned resist 902 is subsequently stripped from the backside of the wafer 900.

Although not specifically shown, a further singulation step may be employed to singulate the ultrasound transducer arrangements 100, e.g. by dicing the sacrificial regions 912. Alternatively, the etch step shown in step (f) may include the removal of the sacrificial regions 912 such that the ultrasound transducer arrangements 100 are individualized in a single step process.

At this point, it is noted that the wafer 900 may of course include further substrate islands, e.g. mounting substrate islands 130 and/or dummy substrate islands 140, which, were necessary, may be connected to the ultrasonic transducer substrate islands or chips 110 and/or the contact substrate islands or chips 120 as explained above for the electrical connection between the contacts 114, 122. These further substrate islands have not been shown for reasons of clarity only.

It is further noted that the contact substrate islands or chips 120 further comprise a plurality of external contacts for connecting the contact substrate islands or chips 120 to coaxial wire assemblies 200 as previously explained. Again, these external contacts may be formed in any suitable manner and have not been shown for reasons of clarity only. In an embodiment, solder bumps may be formed on these external contacts. The solder bumps may be formed on the external contacts at any suitable point in the aforementioned manufacturing process, for instance before or after the singulation of the arrays 520, 530. The solder bumps may be formed on the contacts in any suitable manner, for instance by using a laser process as available from the PacTech Company, Nauen, Germany.

As previously mentioned, the ultrasound transducer arrangement 100 may include passive components 134 such as one or more capacitors, e.g. decoupling capacitors. Such decoupling capacitors are typically necessary if the ultrasound transducer arrangement 100 comprises components that produce switching transients that are large enough to compromise the integrity of the power supply. An example of such a component is a signal processing IC such as an ASIC. This problem is particularly prevalent at a miniature probe tip where the power supply lines tend to have a relatively high and undefined impedance. In such a scenario, decoupling capacitors are used to decouple various components from the power supply lines such that these components are shielded from fluctuations in the power supply. Such decoupling capacitors have capacitances typically ranging from 1 to 100 nF. Furthermore, discrete capacitors may be included to establish an AC connection between different circuit parts operating at different DC potentials, e.g. in the case of a CMUT transducer array and an ASIC. Such a capacitor must be electrically floating, i.e. must be dielectrically insulated from the substrate and ground.

The size of such discrete capacitors is such that integration in a miniaturized ultrasound probe tip is prohibited as such capacitors are simply too big. In an embodiment, this problem is addressed by the integration of trench capacitors in at least some of the substrate islands 110, 120, 130, such that the need for the inclusion of discrete capacitors in the ultrasound transducer arrangement 100 is obviated.

Advantageously, the ultrasound transducer arrangement 100 comprises a plurality of substrate islands at least including a first substrate island 110 comprising a plurality of ultrasound transducer cells 112 and a second substrate island 120 comprising an array of external contacts for connecting the ultrasound sensor arrangement to a flexible tubular body, with the plurality of substrate islands optionally further comprising at least one mounting substrate island 130 for mounting one or more active and/or passive components thereon as previously explained. In an embodiment, at least two of these substrate islands each comprise such a trench capacitor, which has the advantage that the respective trench capacitors are truly electrically isolated from each other due to the fact that they are located in different substrates, such that these different substrates can be operated at different potentials. Moreover, the inclusion of the trench capacitors obviates the need for discrete capacitors to be included in the ultrasound transducer arrangement 100, thereby further aiding the miniaturization of the ultrasound transducer arrangement 100 and an ultrasound probe tip formed from such an arrangement.

In the context of the present application, a trench capacitor is a capacitor formed by a plurality of trenches extending more or less perpendicularly from a major surface of the substrate into the substrate. The trenches may have any suitable shape, e.g. outline, e.g. the trenches may be square, rectangular, circular trenches and so on. The substrate typically is a conducting or semiconducting substrate and acts as the first plate of the trench capacitor. The trenches are typically lined with an electrical insulator, e.g. a dielectric material, and filled with a further conductive or semiconductive material acting as the second plate of the trench capacitor, wherein the electrical insulator separates the first plate from the second plate. Due to the fact that the plates of the trench capacitor extend in all three dimensions and are formed by multiple trenches, a capacitor is obtained that have a large plate area in a compact substrate volume, thereby achieving a compact high capacity capacitor.

Figure 10:
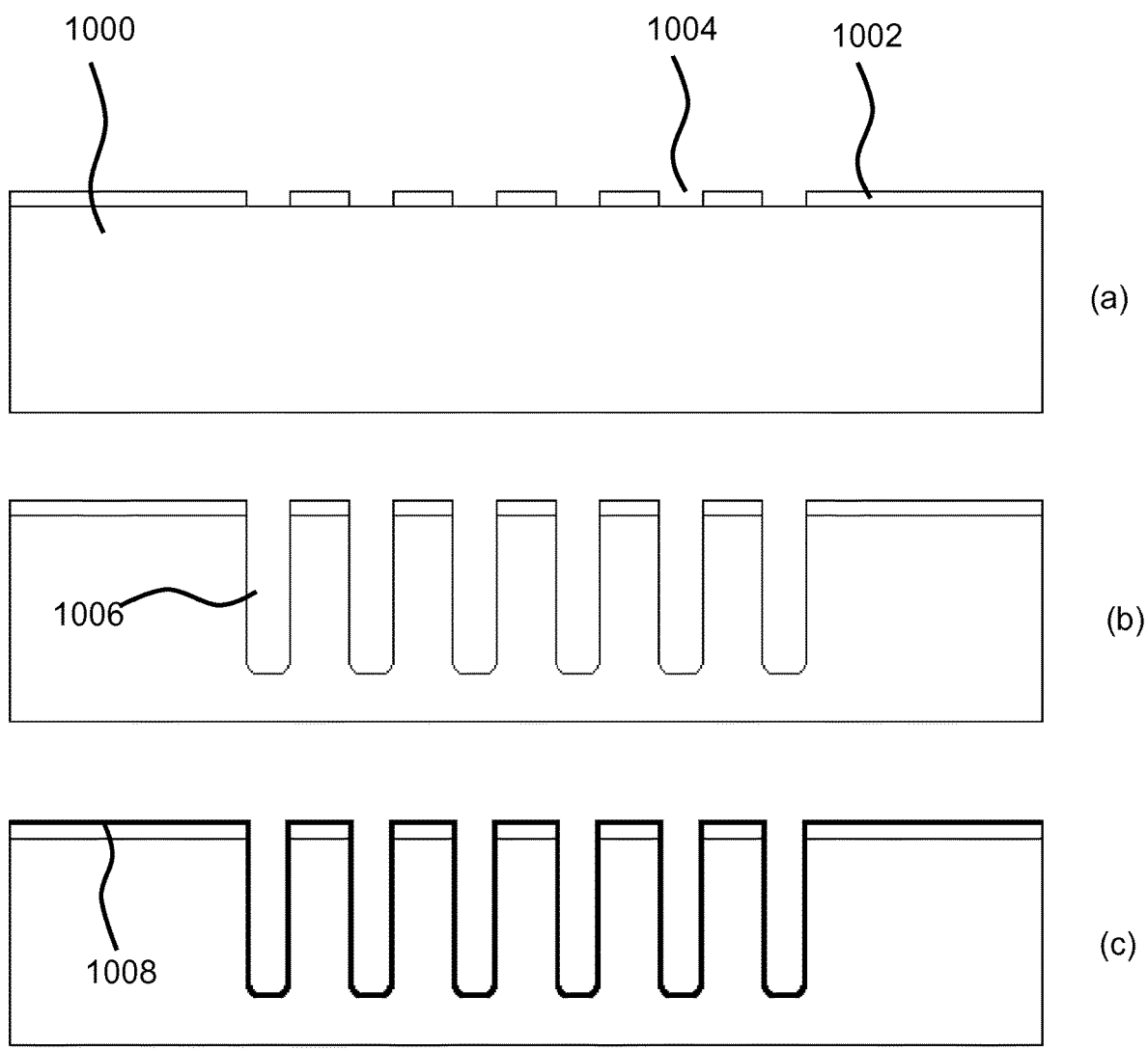
FIG. 10 schematically depicts a method of integrating trench capacitors into an ultrasound transducer arrangement according to an embodiment.
Figure 10:
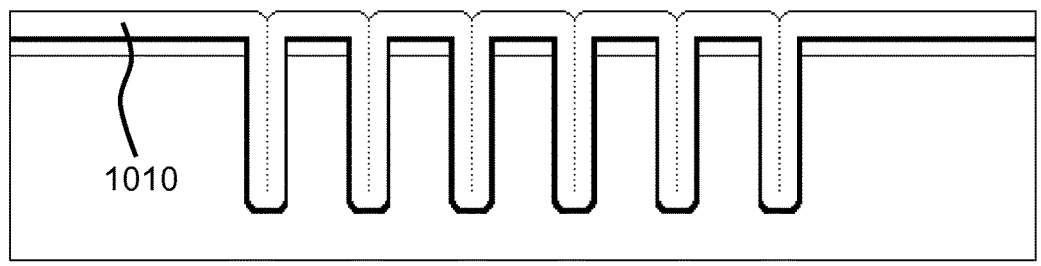
Figure 10:
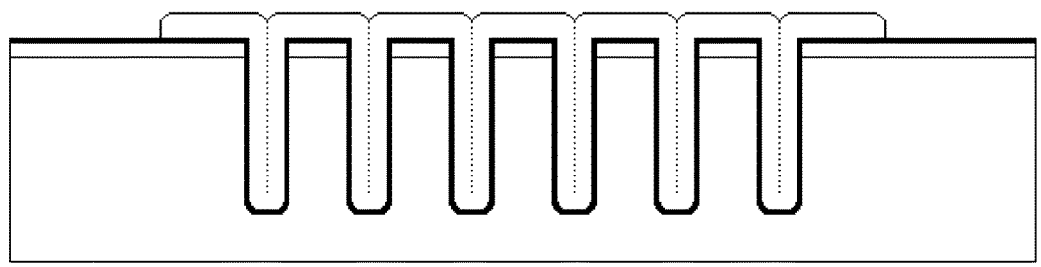
Figure 10:
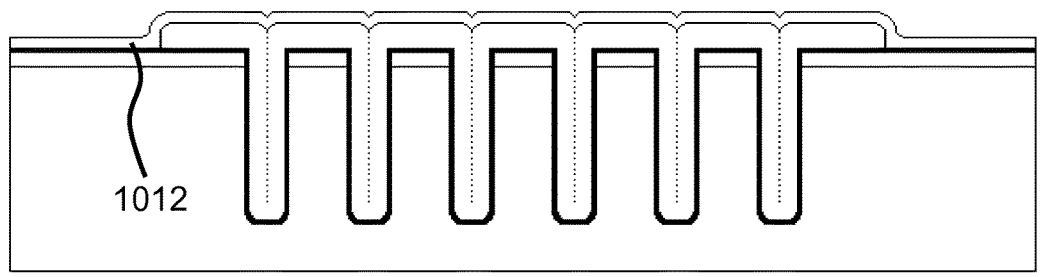
Figure 10:
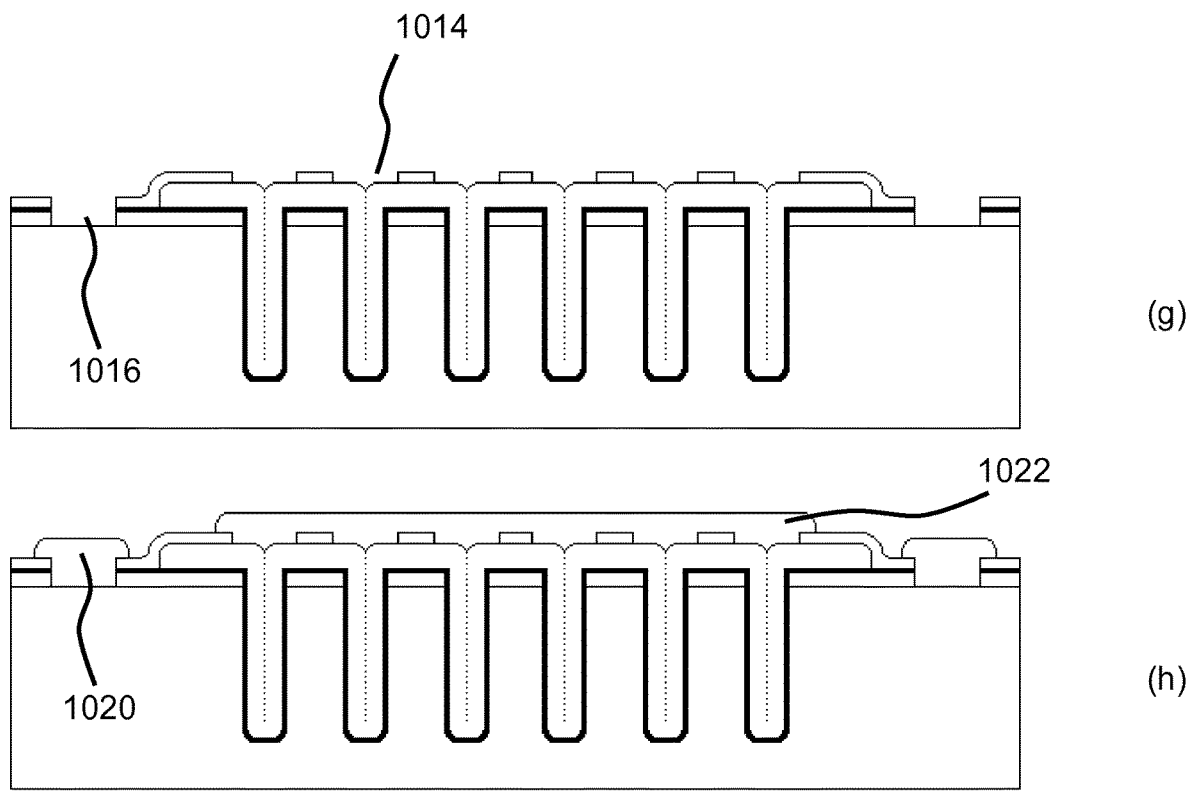

FIG. 10 schematically depicts an example embodiment of a method of manufacturing such a trench capacitor. It should be understood that alternative manufacturing methods are readily available and will be known to the skilled person. Such alternative manufacturing methods may also be contemplated.

The method begins in step (a) with the provision of a conductive substrate 1000, which may be a part of a wafer 900 and may be converted into one of the aforementioned substrate islands 110, 120, 130 as previously explained, for instance with the aid of FIG. 9. The conductive substrate 1000 for instance may be a highly conductive silicon substrate, such as an n-type substrate, e.g. an As-doped substrate although p-type substrates may also be used. Also, substrate materials other than silicon may be contemplated as previously explained. A suitable etch-mask 1002 is formed on the substrate 100 for instance by growing a thermal oxide on the substrate 1000, which thermal oxide is opened to create openings 1004 where the trenches of the trench capacitor are to be formed. The etch-mask 1002 may be formed to any suitable thickness, e.g. about 1 μm.

Next, as shown in step (b), the trenches 1006 are etched using a suitable etch recipe, e.g. using Deep Reactive Ion Etching in case of a silicon substrate 1000. The trenches 1006 may be etched to a depth of about 50-60% of the final thickness of the substrate island to be formed. For instance, for a substrate island having a final thickness of about 50 μm, the trenches 1006 may be etched to a depth of about 30 μm The trenches 1006 may have any suitable width, such as a width of about 1-2 μm.

After etching of the pores 1006, a capacitor dielectric 1008 is deposited in step (c). Any suitable dielectric material may be used for this purpose. A particularly suitable material is silicon nitride, which for instance may be deposited using LPCVD. However, other dielectric materials such as silicon oxide, aluminium oxide or combinations of these materials may also be used, and other deposition techniques, e.g. ALD, may also be contemplated. The capacitor dielectric 1008 may be formed to any suitable thickness, e.g. several tens of nm, e.g. 20 nm.

In step (d), the trenches 1006 lined with the capacitor dielectric 1008 are filled with a conductive material 1010 to form the second plate of the trench capacitor. In an embodiment, the trenches 1006 may be filled by depositing a layer of in-situ doped poly-silicon although other conductive materials may also be used. After patterning the conductive material 1010, e.g. using a suitable etch recipe in step (e), a further dielectric layer 1012 is formed over the patterned conductive material 1010 in step (f) to electrically isolate the conductive material 1010 from subsequent metallization steps. The manufacturing of the trench capacitor is completed by the etching of contact windows 1014, 1016 in step (g) and the deposition and patterning of a metal interconnect layer such as an aluminium interconnect layer in step (h) to form metal contacts 1020 and 1022 to the first plate and second plate of the trench capacitor respectively. As such finalization steps are well-known per se they are not explained in further detail for the sake of brevity only.

As will be clear to the skilled person, the substrate 1000 may be subsequently subjected to further processing steps, e.g. to form an array of transducer elements thereon. For instance, a passivation layer or layer stack may be formed on the trench capacitor after which an array of ultrasonic transducer elements, e.g. CMUT elements may be formed on the passivation layer (stack) as is well known per se. Other further processing steps, e.g. the formation of other elements on such a substrate, will be apparent to the skilled person. It should further be understood that each substrate island may comprise a plurality of such trench capacitors.

Figure 11:
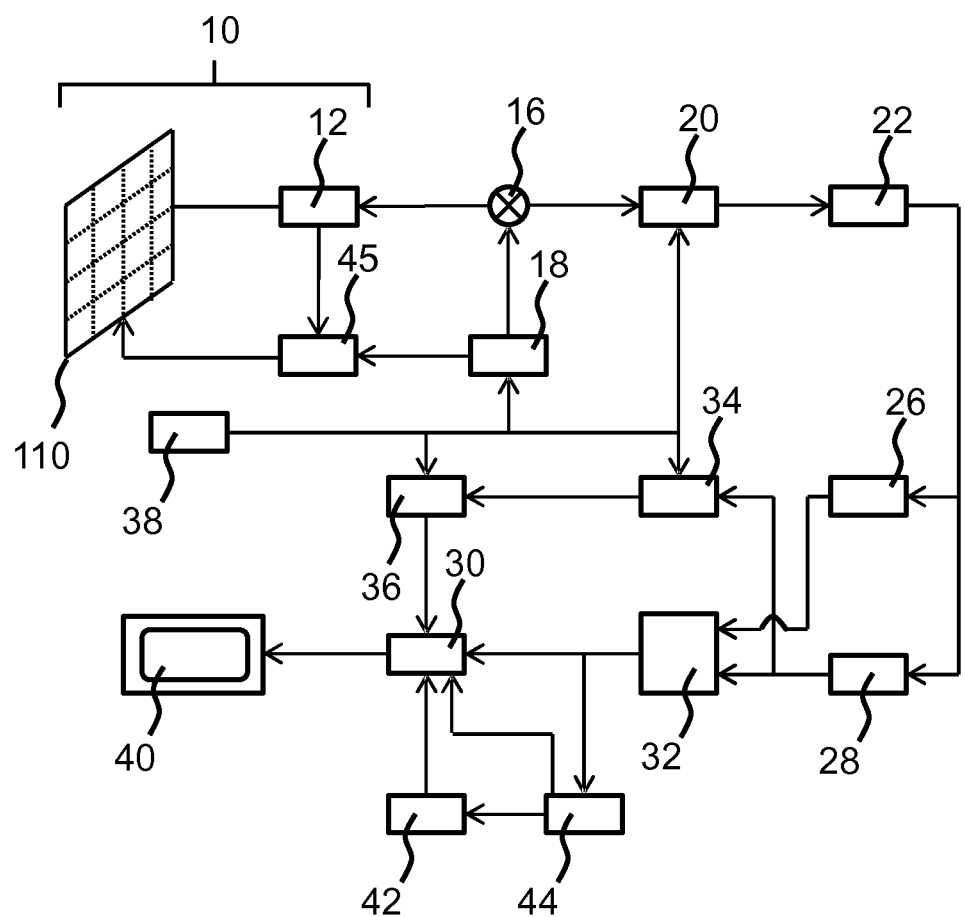
FIG. 11 schematically depicts ultrasonic imaging system according to an example embodiment.

Referring to FIG. 11, an example embodiment of an ultrasonic diagnostic imaging system with an array transducer probe according to an embodiment of the present invention is shown in block diagram form. In FIG. 11 a CMUT transducer array 110 on an ultrasound transducer chip 100 (not shown in FIG. 11) is provided in an ultrasound probe 10 for transmitting ultrasonic waves and receiving echo information. The transducer array 110 may alternatively comprise piezoelectric transducer elements formed of materials such as lead zirconate titanate (PZT) or polyvinylidenefluoride (PVDF). The transducer array 110 may be a one- or a two-dimensional array of transducer elements capable of scanning in a 2D plane or in three dimensions for 3D imaging.

The transducer array 110 is coupled to a microbeam former 12 in the probe 10 which controls transmission and reception of signals by the CMUT array cells or piezoelectric elements. Microbeam formers are capable of at least partial beam forming of the signals received by groups or "patches" of transducer elements for instance as described in U.S. Pat. No. 5,997,479 (Savord et al.), U.S. Pat. No. 6,013,032 (Savord), and U.S. Pat. No. 6,623,432 (Powers et al.).

The microbeam former 12 is coupled by the probe cable, e.g. coaxial wire 410, to a transmit/receive (T/R) switch 16 which switches between transmission and reception and protects the main beam former 20 from high energy transmit signals when a microbeam former is not present or used and the transducer array 110 is operated directly by the main system beam former 20. The transmission of ultrasonic beams from the transducer array 110 under control of the microbeam former 12 is directed by a transducer controller 18 coupled to the microbeam former by the T/R switch 16 and the main system beam former 20, which receives input from the user's operation of the user interface or control panel 38. One of the functions controlled by the transducer controller 18 is the direction in which beams are steered and focused. Beams may be steered straight ahead from (orthogonal to) the transducer array 110, or at different angles for a wider field of view. The transducer controller 18 may be coupled to control a DC bias control 45 for the CMUT array. For instance, the DC bias control 45 sets DC bias voltage(s) that are applied to the CMUT cells 150 of a CMUT array 110.

The partially beam-formed signals produced by the microbeam former 12 are forwarded to the main beam former 20 where partially beam-formed signals from individual patches of transducer elements are combined into a fully beam-formed signal. For example, the main beam former 20 may have 128 channels, each of which receives a partially beam-formed signal from a patch of dozens or hundreds of CMUT transducer cells 112 (see FIG. 1-3) or piezoelectric elements. In this way the signals received by thousands of transducer elements of a transducer array 110 can contribute efficiently to a single beam-formed signal.

The beam-formed signals are coupled to a signal processor 22. The signal processor 22 can process the received echo signals in various ways, such as bandpass filtering, decimation, I and Q component separation, and harmonic signal separation which acts to separate linear and nonlinear signals so as to enable the identification of nonlinear (higher harmonics of the fundamental frequency) echo signals returned from tissue and microbubbles.

The signal processor 22 optionally may perform additional signal enhancement such as speckle reduction, signal compounding, and noise elimination. The bandpass filter in the signal processor 22 may be a tracking filter, with its passband sliding from a higher frequency band to a lower frequency band as echo signals are received from increasing depths, thereby rejecting the noise at higher frequencies from greater depths where these frequencies are devoid of anatomical information.

The processed signals are coupled to a B-mode processor 26 and optionally to a Doppler processor 28. The B-mode processor 26 employs detection of an amplitude of the received ultrasound signal for the imaging of structures in the body such as the tissue of organs and vessels in the body. B-mode images of structure of the body may be formed in either the harmonic image mode or the fundamental image mode or a combination of both for instance as described in U.S. Pat. No. 6,283,919 (Roundhill et al.) and U.S. Pat. No. 6,458,083 (Jago et al.)

The Doppler processor 28, if present, processes temporally distinct signals from tissue movement and blood flow for the detection of the motion of substances, such as the flow of blood cells in the image field. The Doppler processor typically includes a wall filter with parameters which may be set to pass and/or reject echoes returned from selected types of materials in the body. For instance, the wall filter can be set to have a passband characteristic which passes signal of relatively low amplitude from higher velocity materials while rejecting relatively strong signals from lower or zero velocity material.

This passband characteristic will pass signals from flowing blood while rejecting signals from nearby stationary or slowing moving objects such as the wall of the heart. An inverse characteristic would pass signals from moving tissue of the heart while rejecting blood flow signals for what is referred to as tissue Doppler imaging, detecting and depicting the motion of tissue. The Doppler processor receives and processes a sequence of temporally discrete echo signals from different points in an image field, the sequence of echoes from a particular point referred to as an ensemble. An ensemble of echoes received in rapid succession over a relatively short interval can be used to estimate the Doppler shift frequency of flowing blood, with the correspondence of the Doppler frequency to velocity indicating the blood flow velocity. An ensemble of echoes received over a longer period of time is used to estimate the velocity of slower flowing blood or slowly moving tissue.

The structural and motion signals produced by the B-mode (and Doppler) processor(s) are coupled to a scan converter 32 and a multiplanar reformatter 44. The scan converter 32 arranges the echo signals in the spatial relationship from which they were received in a desired image format. For instance, the scan converter may arrange the echo signal into a two dimensional (2D) sector-shaped format, or a pyramidal three dimensional (3D) image.

The scan converter can overlay a B-mode structural image with colors corresponding to motion at points in the image field with their Doppler-estimated velocities to produce a color Doppler image which depicts the motion of tissue and blood flow in the image field. The multiplanar reformatter 44 will convert echoes which are received from points in a common plane in a volumetric region of the body into an ultrasonic image of that plane, for instance as described in U.S. Pat. No. 6,443,896 (Detmer). A volume renderer 42 converts the echo signals of a 3D data set into a projected 3D image as viewed from a given reference point as described in U.S. Pat. No. 6,530,885 (Entrekin et al.)

The 2D or 3D images are coupled from the scan converter 32, multiplanar reformatter 44, and volume renderer 42 to an image processor 30 for further enhancement, buffering and temporary storage for display on an image display 40. In addition to being used for imaging, the blood flow values produced by the Doppler processor 28 and tissue structure information produced by the B-mode processor 26 are coupled to a quantification processor 34. The quantification processor produces measures of different flow conditions such as the volume rate of blood flow as well as structural measurements such as the sizes of organs and gestational age. The quantification processor may receive input from the user control panel 38, such as the point in the anatomy of an image where a measurement is to be made.

Output data from the quantification processor is coupled to a graphics processor 36 for the reproduction of measurement graphics and values with the image on the display 40. The graphics processor 36 can also generate graphic overlays for display with the ultrasound images. These graphic overlays can contain standard identifying information such as patient name, date and time of the image, imaging parameters, and the like. For these purposes the graphics processor receives input from the user interface 38, such as patient name.

The user interface is also coupled to the transmit controller 18 to control the generation of ultrasound signals from the transducer array 110 and hence the images produced by the transducer array and the ultrasound system. The user interface is also coupled to the multiplanar reformatter 44 for selection and control of the planes of multiple multiplanar reformatted (MPR) images which may be used to perform quantified measures in the image field of the MPR images.

As will be understood by the skilled person, the above embodiment of an ultrasonic diagnostic imaging system is intended to give a non-limiting example of such an ultrasonic diagnostic imaging system. The skilled person will immediately realize that several variations in the architecture of the ultrasonic diagnostic imaging system are feasible without departing from the teachings of the present invention. For instance, as also indicated in the above embodiment, the microbeam former 12 and/or the Doppler processor 28 may be omitted, the ultrasound probe 10 may not have 3D imaging capabilities and so on. Other variations will be apparent to the skilled person.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. An ultrasound transducer assembly comprising:
a foldable ultrasound transducer arrangement comprising a plurality of substrate islands spatially separated and electrically interconnected by a flexible polymer assembly including electrically conductive tracks providing said electrical interconnections, wherein the plurality of substrate islands includes a first substrate island comprising a plurality of ultrasound transducer cells and a second substrate island comprising an array of external contacts for connecting the ultrasound sensor arrangement to a flexible tubular body; and
a rigid support structure having a first planar portion at an end of the rigid support structure comprising a first surface and a second surface opposite the first surface, a second planar portion at another end of the rigid support structure having a third surface and a fourth surface opposite the third surface, wherein the second surface and the third surface face each other and extend parallel to one another, and a third planar portion having a fifth surface extending between the second surface and the third surface, wherein the fifth surface is orthogonal to the second surface and the third surface;
wherein the foldable ultrasound arrangement is folded onto the support structure such that the first substrate island is mounted on the first surface and the second island is mounted on the fourth surface.

2. The ultrasound transducer assembly of claim 1, wherein the ultrasound transducer arrangement further comprises at least one further substrate island comprising a plurality of external contacts for receiving active components, passive components, or a combination of active and passive components, wherein the at least one further substrate island is mounted on the third planar portion.

3. The ultrasound transducer assembly of claim 2, further comprising the active components, passive components, or a combination of active and passive components mounted on the at least one further substrate island.

4. The ultrasound transducer assembly of claim 2, wherein at least one of the first substrate island, the second substrate island and the at least one further substrate island further comprises a plurality of trenches defining a decoupling capacitor, each trench being filled by a conductive material separated from the substrate material by an electrically insulating material.

5. The ultrasound transducer assembly of claim 4, further comprising a plurality of the decoupling capacitors, each decoupling capacitor of the plurality being located on a different substrate island.

6. The ultrasound transducer assembly of claim 1, wherein the rigid support structure is a metal support structure.

7. The ultrasound transducer assembly of claim 1, wherein the first substrate island is separated from the first surface by a backing member.

8. The ultrasound transducer assembly of claim 7, wherein at least a part of the flexible polymer assembly extends along an outer surface of the backing member.

9. An ultrasound probe comprising the ultrasound transducer assembly of claim 1, wherein the third planar portion of the ultrasound transducer assembly is aligned with an overall length of the ultrasound probe.

10. An ultrasound probe comprising the ultrasound transducer assembly of claim 1, wherein an overall length from the first substrate island to the second substrate island is less than 10 mm or less than 8 mm.

11. An ultrasound probe comprising the ultrasound transducer assembly of claim 1, a coaxial wire assembly, and a plurality of solder bumps in the coaxial wire assembly, wherein each of the external contacts of the second substrate island is conductively coupled to one of the plurality of solder bumps, and wherein the ultrasound probe is configured to generate echo signals.

12. An ultrasonic imaging system including the ultrasound probe of claim 11 and a processor configured to receive the echo signals from the ultrasound probe and process the echo signals to generate ultrasound images.

* * * * *